United States Patent
Aldal et al.

(10) Patent No.: US 6,672,131 B1
(45) Date of Patent: Jan. 6, 2004

(54) METHOD FOR OPERATING A MEASUREMENT INSTRUMENT

(75) Inventors: Dag Aldal, Fyllingsdalen (NO); Geir Instadnes, Nesttum (NO)

(73) Assignee: Clampon AS, Laksevag (NO)

( * ) Notice: Subject to any disclaimer, the term of this patent is extended or adjusted under 35 U.S.C. 154(b) by 0 days.

(21) Appl. No.: 09/869,943
(22) PCT Filed: Jan. 18, 2000
(86) PCT No.: PCT/NO00/00013
§ 371 (c)(1), (2), (4) Date: Aug. 27, 2001
(87) PCT Pub. No.: WO00/45161
PCT Pub. Date: Aug. 3, 2000

(51) Int. Cl.$^7$ ................................................ G01H 13/00
(52) U.S. Cl. ............................ 73/1.83; 73/1.82; 73/627
(58) Field of Search .................. 73/1.82, 1.83, 73/602, 627, 629, 631

(56) References Cited

U.S. PATENT DOCUMENTS

| | | | |
|---|---|---|---|
| 4,233,849 A | * 11/1980 | Defebvre et al. .............. | 73/812 |
| 4,453,238 A | * 6/1984 | Van Buren .................... | 367/13 |
| 4,838,127 A | * 6/1989 | Herremans et al. ...... | 73/861.28 |
| 5,530,678 A | * 6/1996 | Kosalos ......................... | 367/13 |
| 6,035,696 A | * 3/2000 | Kiefer et al. ................ | 73/1.82 |

FOREIGN PATENT DOCUMENTS

JP 09108223 A * 4/1997 ............ A61B/8/12

* cited by examiner

Primary Examiner—Hezron Williams
Assistant Examiner—Rose M. Miller
(74) Attorney, Agent, or Firm—Francis C. Hand; Carella, Byrne, Bain et al.

(57) ABSTRACT

A description is given of a method for operating a measuring instrument (10) fitted onto the surface (16) of a fluid carrying body (18), in particular a hollow body such as a pipe, which transports multiphase fluid flows, especially fluids containing solid particles, wherein acoustic data related to fractions and amounts of the different phases in the fluid flow are registered. The method is characterized in that the measuring instrunment (10) is calibrated to, continuously or with time intervals, correct for possible alterations in the contact (A) between the measuring instrument (10) and the surface of the pipeline (18), in that the active sensing part (12) is made to transmit a characteristic acoustic signal, the acoustic signal, which is reflected from the surface of the body, is received by the receiving part (14) of the sensor, and optionally the signal is amplified, and the strength of the reflected signal is measured and compared to the strength of the transmitted signal, whereby the amplification of the signal from the passive part (18) of the sensor, dependent on possible alterations in the said contact, is adjusted until a given ratio between the strength of the transmitted and received signals is obtained.

8 Claims, 3 Drawing Sheets

METHOD FOR OPERATING A MEASUREMENT INSTRUMENT

The present invention relates to methods for carrying out measurements of multiphase fluid flow in pipes and ducts, according to the definition in the introduction of the respective subsequent independent claims 1 and 6. There are also disclosed some preferred areas of use of the method according to the invention.

Furthermore, the invention is concerned with measuring the fluid flow rates, the amount of participating particles mixed with fluids, gases etc, or other parameters of the fluids that flow through pipes or ducts in which acoustic sensors are applied, or where safety rules dictate that measuring devices, or parts thereof, can not intrude (completely or partially penetrate through) the pipe or duct.

In connection with production or transport of hydrocarbons (oil, gas and mixtures of these), it may be desirable to measure different parameters of the flow in the pipe. If measurements such as these can be made without making a hole in the pipe wall, i.e. using so called non-intrusive instruments, without special design or modification of standard pipe systems, design and production costs as well as operation costs of the pipe system will be reduced. It will also simplify retrofitting on existing pipes as well as reduce the risk of leakage compared with traditional measuring instruments which require flanges, valves and the like, to get direct access to the flow of fluid in the pipe or the duct.

For example, non-intrusing instruments may be acoustic instruments or temperature probes. For a number years, acoustic, non-intrusing measuring instruments have been known within the oil industry, as well as oil-related industry, to measure amongst other things undesirable fractions of particles such as sand, which may follow the stream of oil and gas.

This type of technology and measuring instruments may also be used in a number of other applications in which fluid, gas and particles, individually, or in an arbitrary combination of these, are being transported through pipes. Illustrative examples are piping systems for transport of coal and water etc, as well as within chemical processing plants. When fluid and particles, individually or in an arbitrary and varying combination of these, are being transported through a pipe, canal or duct, these types of measuring instruments may be applied, as they can be fitted onto one of the outer walls of the duct.

A measuring system which register, with the aid of ultra sound from a passive acoustic sensor, with the aid of its sensing part, the energy that particles in a flow of fluid or gas will emit when they impact the wall of a pipe, is previously known from NO Patent No 301.948. However, it is not possible with a system such as this to determine if the sensor makes satisfactory contact with the pipe wall, and whether this contact changes with time.

Acoustic measuring instruments, operating both in transmitting and receiving modes, and denoted a transducer, operates in a manner so that the transmitter transmits an active pulse which is reflected from the inner surface of the pipe wall, and where the sensor registers the reflected acoustic pulse, are also known. A single transducer (sensor) element, which can alternate between transmission and reception mode, may also be employed. The measuring instruments register the time for the acoustic pulse being transmitted from the transmitter to the reflected pulse being received by the sensor. With knowledge of the speed of sound in the pipe wall, the thickness of the pipe wall can be determined, as well as the possible erosion or corrosion of the pipe wall.

U.S. Pat. No. 5,507,185, discloses ah ultrasonic flow detection system including means for carrying out corrections when the system looses contact (so-called lift-off) with the test object. If such lift-off occurs, a mechanical correction is effected. However, the correction is made by manual operation, i.e. the instrument is moved along the test object by an operator.

Thus, the teaching of the U.S. Pat. No. 5,507,185, is not suitable for applications where the transducer is to be permanent mounted to e.g. an oil/gas conducting pipe on the sea bed, as is the case of the present invention Further, Further, reference is made to the following patent publications: EP-patent No. 0096.338, GS-patent No. 1.413.755, U.S. Pat. Nos. 5,852,232, 3,906,780, 3,854,323, and 3,816,773.

It is an object of the invention to provide for a new method which may compensate for varying contact between a measuring instrument and a fluid carrying pipe.

It is a further object of the invention to provide for a new method for registering the individual fractions of multi phase fluid flows by using a transducer as disclosed above.

The methods according to this invention are identified by the aspects, which are noted in the characteristics of the thereinafter independent claims 1 and 7 respectively. Preferred embodiments of the methods, according to the present invention, is described in the dependent claims for the methods.

According to the invention, the method(s) are applied according to the aforementioned claims for the methods of registering the fraction of sand in water that is containing sand, as a consequence of erosion, for example in rivers from glaciers and the like. In a river that carries particles as a result of erosion, such as rivers from glaciers, the instrument may be fitted to the underside of a plate, which is placed in the river such that the water containing the particles is flowing over the other surface of the plate, or a representative side stream of the water is brought to flow through a pipe wherein the instrument is fitted to the pipe surface.

According to a preferred application, the software in one or more of the microprocessors which are fitted to in the sensing part of the instrument, may be overwritten, deleted or altered by a new program or new settings/adjustments being transmitted via the sensor signal or power connection.

The invention will be explained further in the following with reference to the following figures, wherein.

Figure 1A:
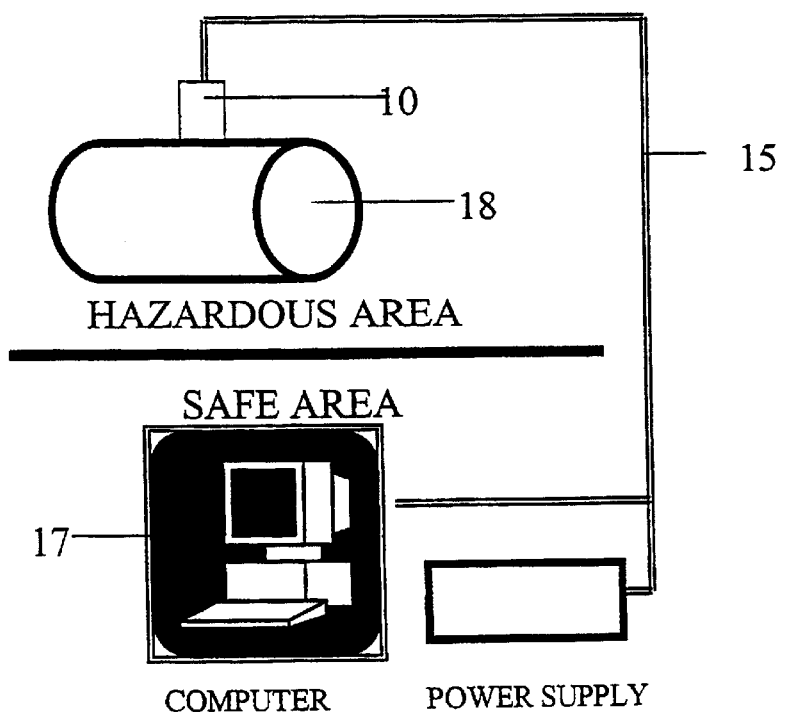
FIG. 1A shows a schematic view of a measuring instrument, which is fitted to a pipe and encompasses an ultrasound sensor and electronics card for registering the data.

FIG. 1A shows schematically the measuring instrument fitted onto a pipe 18, encompassing an ultrasensor 10 and housing wherein an electronics card for recording data is inserted. The ultrasound sensor 10 is connected to the electronics card. Cables 15, (for example fibre optics or another type) run from the electronics card, transferring the signals from the electronics cards to a computer (PC) 17 (for example, with supporting keyboard and screen), or another computer which processes the data and displays the results. The electronics card for the passively listening ultrasound sensor encompasses a filter unit (cf. FIG. 7 in the aforementioned NO-301.948), which functions as an adapter module for the sensor with a tuned frequency. An amplification step 22 (FIG. 2) with band-pass filter 20 is a unit which performs a raw amplification within a given frequency range. The amplification step with programmable amplification performs amplification controlled by a microprocessor, depending on the noise level. A converter converts analogue signals to digital signals. A microprocessor processes the data, determines amplification and transmits data. A data transmission unit transmits the data to the computer via the transmission cable 17 on FIG. 1A.

Figure 1B:
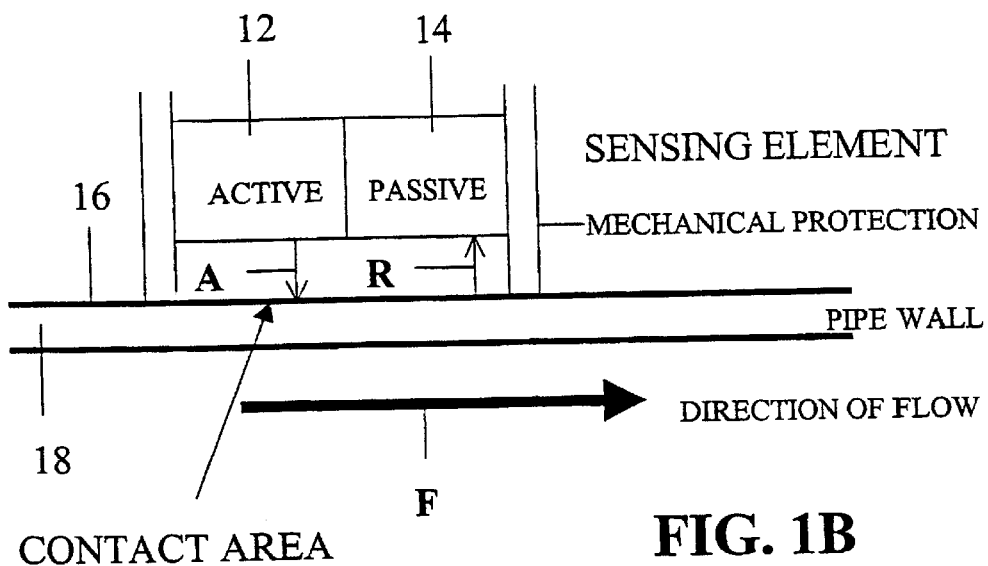
FIG. 1B shows a schematic cross-section view of a sensor element fitted onto the surface of a pipe (half, the pipe is shown in a side section view).

The sensor 10 encompasses an active and a passive part 12, 14 which are fitted such that they make contact with the outer wall 16 of a pipeline 18, which is shown in a longitudinal cross-section in FIG. 1B. The direction of flow for the fluid may be as shown by the arrow F. It is indicated with the arrows A and R respectively, that the active sensor part 12 transmits acoustic signals to the surface 16 of the pipe 18, and that the passive sensor part 12 receives the reflected acoustic signals from the surface. The reference R may also represent the acoustic signals arising from the fluid (multiphase) which is flowing through the pipe.

Figure 2:
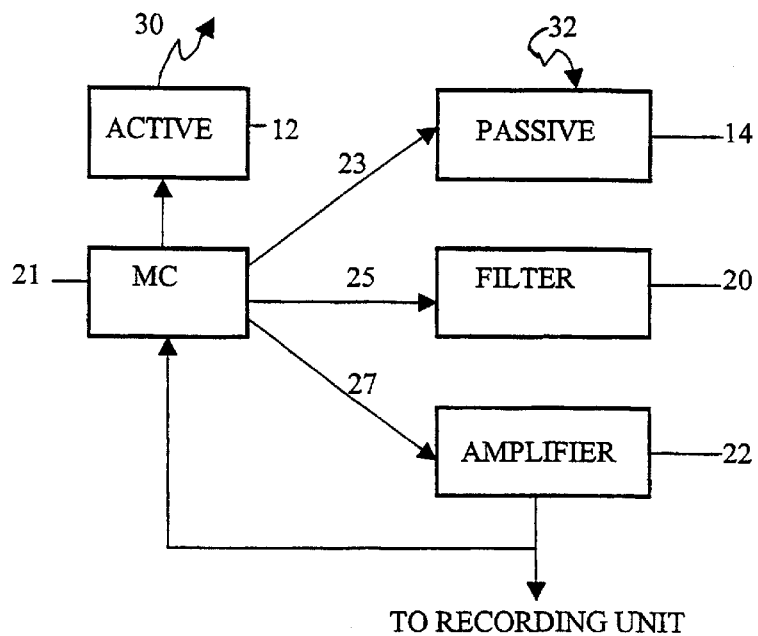
FIG. 2 shows a schematic block diagram of the connections for the sensor element according to the invention.

A schematic block diagram for connecting the sensor element according to the present invention, is shown in FIG. 2. The active part 12 of the transmission unit is connected to, and controlled by, a data unit 21 (MC), which also controls the passive receiver 14, as well as a filter 20 and an amplifier 22, shown with the interconnecting lines 23,25 and 27.

The data unit 21 is instructing the active transmitter 12 to send an acoustic signal 30 towards the pipe wall. A part of the acoustic signal 30 continues through the pipe wall 18, while a part is reflected from the surface 16 of the pipe 18 as the signal 32, which is then picked up and registered by the passive listening sensor 14. The data unit is designed to register the reflected signal via the line 23. From the sensor 14, the signal is sent on to the filter and further on to the amplifier 22, which transmits a signal to a monitoring unit or some other unit. According to the invention, the signal from the amplifier is predominantly a given ratio between the transmitted signal and the received signal.

Figure 3:
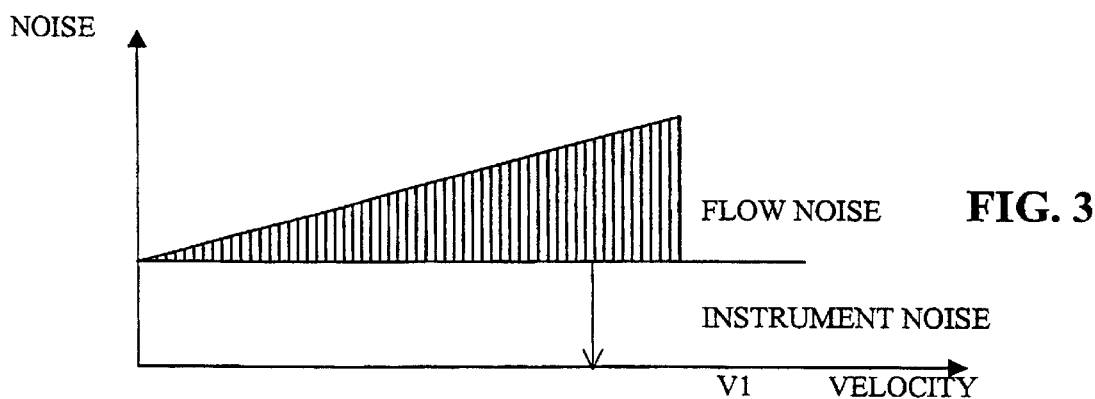
FIG. 3 shows a diagram of the registration of noise by the sensor as a function of the noise from the instrument itself and noise which stems from the flow rate of a fluid flowing through a pipe.

FIG. 3 shows a diagram of the registration of noise by the sensor 14 as a function of the noise from the instrument itself, and noise arising from the flow rate of a fluid flowing through a pipe. It can be seen that the noise from the instrument is predominantly constant and not influenced by the fluid flow rate. The noise from the flowing fluid does, however, increase with the flow rate of the fluid. Similarly, the noise generated by solid particles (sand) will increase proportionally with the flow rate of the sand/fluid.

Figure 4:
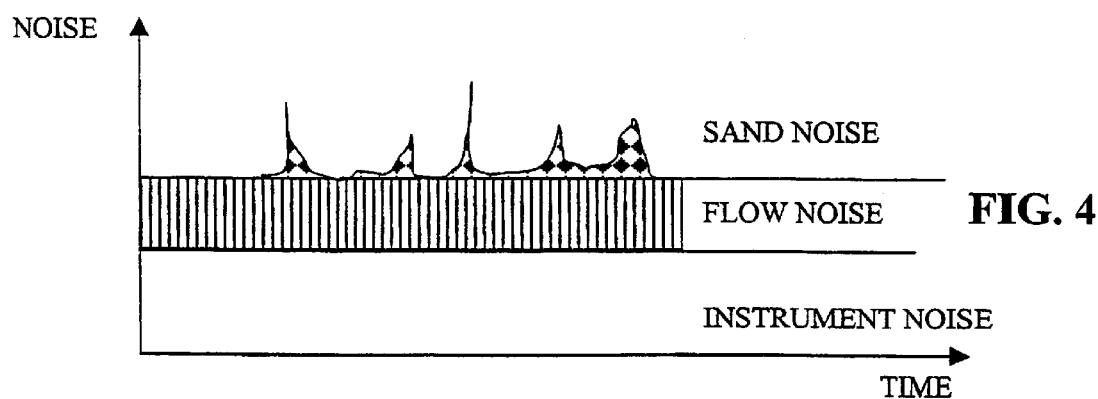
FIG. 4 shows a diagram of the registration by the sensor of noise from the sand, noise from the flow and noise from the instrument itself as a function of the time taken for a given arbitrary measurement.

FIG. 4 shows a diagram of the registration by the sensor of noise from the sand, noise from the flowing fluid and noise from the instrument itself, as a function of time for a given arbitrary measurement. Over the measured time period on the diagram, stable amounts and volumes of flow is assumed to run through the pipe. The constant instrument noise and noise from the flowing fluid are clearly indicated, together with noise from the sand in the form of peaks, something which indicates that the amount of sand varies much over the time period.

Figure 5:
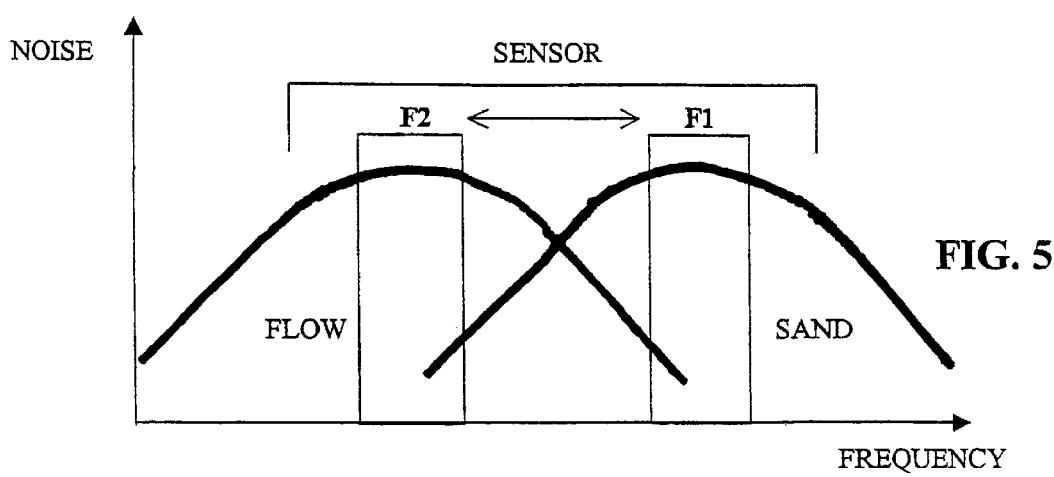
FIG. 5 shows a diagram of the course of noise over a given frequency range for the flow itself and for the sand particles.

FIG. 5 shows a diagram of the progress of noise over a given frequency range for the flow itself and for the sand particles. The curve shows the frequencies at which the two sources of noise will give the predominant noise deflection. The two frequency bands F1 and F2 are showing as an example the bands to which the sensor may be tuned for listening, and between which the listening may alternate, as given according to the invention.

DETAILED DESCRIPTION OF AN EMBODIMENT ACCORDING TO THE INVENTION

The further description refers to a typical application of the invented measuring instrument on a pipe through which oil, water, gas or a combination of these components are flowing, and where there is a need to measure the amount of sand passing by the sensor. This does not exclude application of the invention in other contexts where multi-phase fluids are transported, for example other processing industries, coal fired power stations or water pipe systems. Further, the invention may be applied to determine the amount of any kind of particle flowing through a pipe, a duct or a river, or for example sand particles together with oil and/or gas, which flows up from an oil well through a pipe.

It is of paramount importance for the instrument to make good contact with the pipe wall to determine the amount of particles passing through the pipe, and it is also essential that the acoustic contact is equally good throughout the measuring period. The contact between the pipe wall and the sensor has earlier been verified by, for example, rubbing sandpaper or a file against the pipe wall, with the signal being registered in the measuring instrument. This signal will vary according to the type of sandpaper or file that is used, where on the pipe wall the rubbing takes place, how strong the rubbing is, who is carrying out the rubbing and so on. A control of the acoustic contact such as this, may in reality only be carried out during installation, maintenance, or is effected only when the measuring system is suspected to be faulty. Any improvement of the contact between the measuring instrument and the pipe, which may be located at the sea bed, will lead to an extensive and costly operation. It is an objective of this invention to provide a method with which this problem may be eliminated.

The present invention encompasses a method for imposing a signal with known amplitude (power), to allow comparative tests to be carried out. The measuring instrument encompasses devices for adjusting the amplification of the received signal, such that the response of the measuring instrument to a given imposed signal, for example from the active sensor, may be adjusted to a set level.

Thus, the present invention comprises a method for controlling the contact with regular intervals, such that possible changes in the contact between the measuring instrument and the pipe may be discovered and accounted for, at an early stage.

For example, the contact between the sensor and the pipe weakens if the sensor gets loose from the pipe because of vibration. On the other hand, when the temperature of the fluid in the pipe increases, the pipe wall will expand and the contact pressure of the sensor against the pipe will increase accordingly.

A measuring instrument for registering the aforementioned conditions, comprises an active sensor for transmission of acoustic signals, and a passive sensor for reception of acoustic signals. In an alternative embodiment of the invention, the active (for transmission) and the passive (for reception) parts of the sensor may be arranged in one and the same sensor. In another alternative embodiment of the invention, the one and same sensor may be considered to function at times as an active sensor and at times as a passive sensor.

One or more electrical pulses with known characteristics and amplitude may be imposed on the active sensor. A microprocessor controls the imposition of pulses, and different pulses may be selected as required. When an electrical pulse is imposed on the sensor, the sensor will start to oscillate in response to the imposed pulse. These oscillations are transmitted as pressure-wave signals (ultra sound signals) from the sensor, through eventual protective layers and through the pipe wall. Because of different acoustic characteristics in the different layers (different index of refraction), the transmitted pulse will be reflected from the boundary surface between the different layers.

The reflected pulse will travel in the opposite direction to the transmitted pulse, and be detected by the passive sensor. When an acoustic signal (oscillations) is imposed on this sensor, the sensor will generate an electrical signal that corresponds to the imposed acoustic pulse. According to the invention, this electrical signal is transmitted to a microprocessor and an adjustable amplifier. The microprocessor compares the transmitted pulse with the received pulse, and determines thereafter the amplification adjustments to obtain the desired ratio (an initial set value) between transmitted and received signal.

If a control of the acoustic contact to the pipe can be carried out with a microprocessor, as shown in the present invention, the microprocessor may also be set up to monitor and optionally adjust the contact against the pipe wall at regular time intervals. Monitoring and adjustment may be carried out in a very short time and will to a very small extent influence the continuous monitoring of the flow of particles in the pipe.

According to a particularly preferred embodiment of the method according to the invention, a wide-band passive sensor is connected to the instrument electronics. The signal from the sensor is connected to one or more frequency filters, having a narrower band width than the band width of the sensor. The high pass and low pass frequencies limits for these filters are set by the microprocessors, and thus both the band width and center-frequency for the filters may be adjusted by the microprocessor.

When traditional filters are used, the frequencies are set by selection of electrical components, and when these components are mounted a possible alteration of the filter characteristics will lead to considerably more work, and cannot be carried out without dismantling the measuring instrument. As the filters are so called digital filters, the filter characteristics may be programmed into a microprocessor, by a suitable programming of this, reference is made to the aforementioned text. This means that the receiving frequencies (frequency width) in the measuring instrument which is fitted onto a pipe on the sea bed, may be altered by programming from the topside, i.e. without any form of physical reconnection or replacement of the instrument.

By altering the receiver frequencies for the filters over time, different parts of the frequency spectrum may be measured. It is therefore possible to adjust the filters in such a way that the frequency for the signal under investigation passes through the filter, while signals from other undesirable frequencies (noise) are rejected. If the microprocessor can be programmed via power- or signal lines after the sensor has been installed, the filters may be adjusted such that the sensor is most sensitive in the frequency range in which the signal from the sand is the strongest for the said installation, and wherein undesirable noise is filtered out. This will give a considerable better signal/noise ratio, which in turn will lead to a better measurement result.

As an example, it may be mentioned that different particle sizes of the sand, different flow compositions, different flow rates or different pipe configurations, may lead to the frequency for the said signal being altered.

The acoustic-measuring instrument, according to the invention, measures the signal being generated by the sand in a frequency range. This signal is then converted to a known amount of sand by the formula:

$$M=(S-B)/K$$

Where M=amount of sand in grams;

K=conversion factor for the signal (noise) from sand;

S=sand generated noise, and

B=background noise

Background noise is defined as noise generated by the noise from the flow plus noise from the sensor and electronics. The noise from the sensor and electronics is unique for each measuring instrument, and may be measured under controlled conditions during manufacture of the measuring instrument. The noise generated by the flow is independent of the flow rate.

Noise from the flow is defined as the noise (the signal), generated within a frequency range by the flow through the pipe of, for example, oil, water, gas, or an arbitrary mixture of these components. For a given mixture of oil, water and gas, the noise from the flow will increase with increasing flow rate. There are exceptions to this rule, but they must be regarded as special cases, and are of no interest to the general description of the present invention.

Another advantage with a microprocessor controlling the, filter frequencies is that the filter characteristics may be altered rapidly. Thus, a narrow band-pass filter may be tuned for a short period to the frequency range where the noise from the sand dominates, and subsequently place the filter in the middle of the range in which, for example, the noise from the flow dominates. This has two advantages:

A. Actual noise generated by the flow may be measured.

B. Possible increase in noise generated by the flow indicates an increase in the flow rate.

It is well known that the noise from the flow is determined by means of spot tests, or by the measuring system, either manually or automatically, obtaining from other measuring systems information about the flow rate, and the flow rate is then converted to (expected) noise from the flow. By measuring noise generated by the flow in true time, the factor B in the formula is determined with greater accuracy, and to determine the noise generated by the flow rate, manual or automatic information regarding the flow rate from other measuring instruments will not be required.

The conversion factor K for ratio of an amount of sand and the signal being generated by a this amount of sand, will increase with increasing sand velocity. At higher velocity, the energy of the sand particles will be greater:

$$E=kmv^2$$

where;

E=kinetic energy;

k=a constant;

m=mass of the particles;

v=velocity of the particles.

It is known that the measuring system gets information about the flow rate, either manually or automatically, from other measuring systems, and that the flow rate is subsequently converted to (expected) conversion factor K for the connection between noise generated by the sand and a known amount of sand. By measuring the variations in noise generated by the flow, it will be possible to simultaneously obtain information about variations in flow rate, and this may be used to calculate the conversion factor K for the actual rate. Thus, manual or automatic information from other measuring systems about the flow rate is not necessary to determine the conversion factor K.

The flow rate and the noise generated by the flow, will in most cases vary slowly compared with variations in noise generated by the sand. In a preferred embodiment of the invention, the frequency filters are controlled in such a way that the center frequencies for the filters are set to noise generated by the sand for a substantial part of the time (for example, 95% of the time), while the center frequencies for the frequency filters are set to noise generated by the flow for a minor part of the time (for example, 5%).

What is claimed is:

1. A method of operating a measuring instrument having at least one acoustic sensor in contact with a surface of a fluid carrying body, said method comprising the steps of transmitting an acoustic signal from the sensor onto the surface of the fluid carrying body;

receiving a reflected acoustic signal from the surface of the fluid carrying body;

comparing the received signal with the transmitted signal to determine a ratio between the received signal and the transmitted signal; and thereafter adjusting the received signal to obtain a predetermined ratio between the received signal and the transmitted signal.

2. A method as set forth in claim 1 wherein said predetermined ratio functions as an initial set value representative of an initial contact between the sensor and the fluid carrying body.

3. A method as set forth in claim 1 wherein the amplitude of the received signal is measured and compared to the amplitude of the transmitted signal to determine said ratio and the amplitude of the received signal is adjusted to obtain said predetermined ratio.

4. A method as set forth in claim 1 which further comprises the steps of filtering the frequency of the received signal to register for fractions and amounts of the different phases in a fluid flow and individually adjusting the band width and center frequency of the filter to alternate between frequency ranges in which the noise of different phases are dominant.

5. A method as set forth in claim 4 wherein a plurality of filters are arranged to alternate between a frequency range in which the noise from a flow is dominant and a frequency range in which the noise from particles in the flow is dominant.

6. A measuring instrument comprising a sensor for contacting a surface of a fluid carrying body, said sensor having an active part for transmitting an acoustic signal onto the surface of the fluid carrying body and a passive part for receiving a reflected acoustic signal from the surface of the fluid carrying body; and a microprocessor for comparing the received signal with the transmitted signal to determine a ratio between the received signal and the transmitted signal and thereafter adjusting the received signal to obtain a predetermined ratio between the received signal and the transmitted signal.

7. A measuring instrument as set forth in claim 6 which further comprises an amplifier for amplifying the received signal from said passive part and emitting a corresponding signal to a monitoring unit, said corresponding signal representing said predetermined ratio between the received signal and the transmitted signal.

8. A measuring instrument as set forth in claim 7 which further comprises a frequency filter between said passive part and said amplifier for filtering out selected frequency ranges from the signal passing from said passive part to said amplifier.

* * * * *

UNITED STATES PATENT AND TRADEMARK OFFICE
CERTIFICATE OF CORRECTION

PATENT NO. : 6,672,131 B1
DATED : January 6, 2004
INVENTOR(S) : Aldal et al.

It is certified that error appears in the above-identified patent and that said Letters Patent is hereby corrected as shown below:

Column 1,
Line 51, cancel ","

Column 2,
Line 1, change "ah" to -- an --
Line 11, cancel "Further,"

Signed and Sealed this

Ninth Day of March, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,672,131 B1 Page 1 of 1
APPLICATION NO. : 09/869943
DATED : January 6, 2004
INVENTOR(S) : Aldal et al.

It is certified that error appears in the above-identified patent and that said Letters Patent is hereby corrected as shown below:

In the front page add
(30) Foreign Application Priority Data
January 18, 1999 (NO) 1999 0206

Signed and Sealed this

Thirtieth Day of January, 2007

JON W. DUDAS
*Director of the United States Patent and Trademark Office*